(12) United States Patent
Chang

(10) Patent No.: US 10,220,206 B2
(45) Date of Patent: *Mar. 5, 2019

(54) SYSTEM AND METHOD FOR RELIEVING HYPERTENSION

(71) Applicant: Wen-Chieh Chang, Taichung (TW)

(72) Inventor: Wen-Chieh Chang, Taichung (TW)

(73) Assignee: Taiwan Resonant Waves Research Corp., Taipei (TW)

(*) Notice: Subject to any disclaimer, the term of this patent is extended or adjusted under 35 U.S.C. 154(b) by 130 days.

This patent is subject to a terminal disclaimer.

(21) Appl. No.: 15/345,503

(22) Filed: Nov. 7, 2016

(65) Prior Publication Data

US 2018/0015283 A1    Jan. 18, 2018

(30) Foreign Application Priority Data

Jul. 12, 2016   (TW) .............................. 105121916 A

(51) Int. Cl.
*A61N 1/36* (2006.01)
*A61N 1/04* (2006.01)

(52) U.S. Cl.
CPC ....... *A61N 1/36014* (2013.01); *A61N 1/0492* (2013.01); *A61N 1/36117* (2013.01)

(58) Field of Classification Search
CPC .......................... A61N 1/36014; A61N 1/0492
USPC ........................................................... 607/44
See application file for complete search history.

(56) References Cited

U.S. PATENT DOCUMENTS 9,421,368 B2 *   8/2016   Chang ................ A61N 1/37247
2016/0022989 A1 *   1/2016   Pfeifer ................ A61N 1/0492
435/173.6

* cited by examiner

*Primary Examiner* — Carl H Layno
*Assistant Examiner* — Erin M Piateski

(57) ABSTRACT

A system and method for relieving hypertension includes an energy wave generator set an energy wave's frequency control mode for controlling and generating energy waves with correspond energy densities in multiple energy wave generation periods to effect on a body with hypertension, so as to relieve hypertension by the specific energy wave.

18 Claims, 7 Drawing Sheets

| Order | Freq. | Duty | Phase | Time | Signal Type | | | | | Width | TT | | SUM | | | | Lower | Upper | <Lower | >Upper |
|---|---|---|---|---|---|---|---|---|---|---|---|---|---|---|---|---|---|---|---|---|
| n | Fn(hz) | D(%) | Rote(hz) | T(sec) | SF | SD | SI | SC | SE | m | (sec) | ED | Norm | ED | Avg | filter | limit | limit | limit | limit |
| 1 | 18122 | 70 | 1 | 7 | 1 | | | | | 0 | 7 | 5 | 1.80% | 5 | 5 | 1 | 2.47 | 6.19 | 1.45 | 8.45 |
| 2 | 10000 | 70 | 1 | 15 | 1 | | | | | 0 | 15 | 5 | 1.90% | 5 | 5 | 1 | 2.51 | 6.28 | 1.52 | 8.52 |
| 3 | 7344 | 70 | 1 | 19 | 1 | | | | | 0 | 19 | 5 | 1.90% | 5 | 5 | 1 | 2.49 | 6.24 | 1.49 | 8.49 |
| 4 | 5000 | 70 | 1 | 24 | 1 | | | | | 0 | 24 | 4.9 | 1.80% | 5 | 4.9 | 1 | 2.46 | 6.16 | 1.42 | 8.42 |
| 5 | 4200 | 70 | 1 | 26 | 1 | | | | | 0 | 26 | 4.9 | 1.80% | 5 | 4.9 | 1 | 2.44 | 6.1 | 1.38 | 8.38 |
| 6 | 3672 | 70 | 1 | 28 | 1 | | | | | 0 | 28 | 4.9 | 1.80% | 5 | 4.9 | 1 | 2.43 | 6.07 | 1.36 | 8.36 |
| 7 | 3175 | 70 | 1 | 10 | | 2 | | | | 2 | 30 | 5.3 | 2.00% | 5 | 5.3 | 0 | 0 | 0 | 1.8 | 8.8 |
| 8 | 3000 | 70 | 1 | 31 | 1 | | | | | 0 | 31 | 4.8 | 1.80% | 5 | 4.8 | 0 | 0 | 0 | 1.31 | 8.31 |
| 9 | 2127 | 70 | 1 | 18 | | 2 | | | | 1 | 36 | 5 | 1.90% | 5 | 5 | 1 | 2.52 | 6.29 | 1.53 | 8.53 |
| 10 | 2112 | 70 | 1 | 35 | 1 | | | | | 0 | 35 | 4.7 | 1.80% | 5 | 4.7 | 1 | 2.36 | 5.89 | 1.21 | 8.21 |
| 11 | 2007 | 70 | 1 | 2 | | | | 4 | | 7 | 30 | 5.8 | 2.20% | 6 | 5.8 | 1 | 2.9 | 7.25 | 2.3 | 9.3 |
| 12 | 1865 | 70 | 1 | 37 | 1 | | | | | 0 | 37 | 4.7 | 1.70% | 5 | 4.7 | 1 | 2.34 | 5.85 | 1.18 | 8.18 |
| 13 | 1850 | 70 | 1 | 37 | 1 | | | | | 0 | 37 | 4.7 | 1.70% | 5 | 4.7 | 1 | 2.34 | 5.85 | 1.18 | 8.18 |
| 14 | 1550 | 70 | 1 | 39 | 1 | | | | | 0 | 39 | 4.6 | 1.70% | 5 | 4.6 | 1 | 2.31 | 5.78 | 1.13 | 8.13 |
| 15 | 1234 | 70 | 1 | 42 | 1 | | | | | 0 | 42 | 4.6 | 1.70% | 5 | 4.6 | 1 | 2.28 | 5.7 | 1.06 | 8.06 |
| 16 | 1043 | 70 | 1 | 44 | 1 | | | | | 0 | 44 | 4.5 | 1.70% | 5 | 4.5 | 1 | 2.25 | 5.63 | 1.01 | 8.01 |
| 17 | 1000 | 70 | 1 | 45 | 1 | | | | | 0 | 45 | 4.5 | 1.70% | 5 | 4.5 | 0 | 0 | 0 | 1 | 8 |
| 18 | 921 | 70 | 1 | 15 | | | 3 | | | 2 | 45 | 4.9 | 1.80% | 5 | 4.9 | 0 | 0 | 0 | 1.44 | 8.44 |
| 19 | 880 | 70 | 1 | 47 | 1 | | | | | 0 | 47 | 4.5 | 1.70% | 4 | 4.5 | 1 | 2.23 | 5.58 | 0.96 | 7.96 |
| 20 | 867 | 70 | 1 | 23 | | 2 | | | | 1 | 46 | 4.8 | 1.80% | 5 | 4.8 | 1 | 2.37 | 5.93 | 1.25 | 8.25 |
| 21 | 807 | 70 | 1 | 3 | | | | 4 | | 7 | 45 | 5.6 | 2.10% | 6 | 5.6 | 1 | 2.79 | 6.98 | 2.08 | 9.08 |
| 22 | 778 | 70 | 1 | 3 | | | | 4 | | 9 | 57 | 5.8 | 2.10% | 6 | 5.8 | 1 | 2.89 | 7.21 | 2.27 | 9.27 |
| 23 | 751 | 70 | 1 | 49 | 1 | | | | | 0 | 49 | 4.4 | 1.60% | 4 | 4.4 | 1 | 2.21 | 5.51 | 0.91 | 7.91 |
| 24 | 730 | 70 | 1 | 3 | | | | 4 | | 7 | 45 | 5.5 | 2.10% | 6 | 5.5 | 1 | 2.77 | 6.92 | 2.04 | 9.04 |
| 25 | 705 | 70 | 1 | 12 | | 2 | | | | 3 | 48 | 5 | 1.80% | 5 | 5 | 1 | 2.49 | 6.22 | 1.48 | 8.48 |
| 26 | 668 | 70 | 1 | 6 | | | 3 | | | 8 | 54 | 5.4 | 2.00% | 5 | 5.4 | 0 | 0 | 0 | 1.86 | 8.86 |
| 27 | 652 | 70 | 1 | 5 | | | | 4 | | 5 | 55 | 5.4 | 2.00% | 5 | 5.4 | 0 | 0 | 0 | 1.94 | 8.94 |
| 28 | 625 | 70 | 1 | 9 | | 2 | | | | 5 | 54 | 5.2 | 1.90% | 5 | 5.2 | 0 | 0 | 0 | 1.65 | 8.65 |
| 29 | 612 | 70 | 1 | 51 | 1 | | | | | 0 | 51 | 4.3 | 1.60% | 4 | 4.3 | 1 | 2.17 | 5.42 | 0.84 | 7.84 |
| 30 | 595 | 70 | 1 | 9 | | | 3 | | | 5 | 54 | 5.1 | 1.90% | 5 | 5.1 | 1 | 2.57 | 6.41 | 1.63 | 8.63 |
| 31 | 542 | 70 | 1 | 3 | | | | 4 | | 9 | 57 | 5.6 | 2.10% | 6 | 5.6 | 1 | 2.81 | 7.02 | 2.11 | 9.11 |
| 32 | 522 | 70 | 1 | 53 | 1 | | | | | 0 | 53 | 4.3 | 1.60% | 4 | 4.3 | 1 | 2.14 | 5.36 | 0.79 | 7.79 |
| 33 | 484 | 70 | 1 | 11 | | | 3 | | | 4 | 55 | 5 | 1.80% | 5 | 5 | 1 | 2.48 | 6.21 | 1.47 | 8.47 |
| 34 | 462 | 70 | 1 | 14 | | 2 | | | | 3 | 56 | 4.9 | 1.80% | 5 | 4.9 | 1 | 2.43 | 6.07 | 1.36 | 8.36 |
| 35 | 435 | 70 | 1 | 6 | | | 3 | | | 9 | 60 | 5.3 | 2.00% | 5 | 5.3 | 1 | 2.63 | 6.58 | 1.76 | 8.76 |
| 36 | 421 | 70 | 1 | 14 | | 2 | | | | 3 | 56 | 4.8 | 1.80% | 5 | 4.8 | 0 | 0 | 0 | 1.32 | 8.32 |
| 37 | 380 | 70 | 1 | 12 | | | 3 | | | 4 | 60 | 4.9 | 1.80% | 5 | 4.9 | 0 | 0 | 0 | 1.4 | 8.4 |
| 38 | 348 | 70 | 1 | 5 | | | | 4 | | 5 | 55 | 5.2 | 1.90% | 5 | 5.2 | 0 | 0 | 0 | 1.67 | 8.67 |
| 39 | 302 | 70 | 1 | 20 | | 2 | | | | 2 | 60 | 4.6 | 1.70% | 5 | 4.6 | 1 | 2.29 | 5.73 | 1.08 | 8.08 |
| 40 | 160 | 70 | 1 | 23 | | | 3 | | | 2 | 69 | 4.4 | 1.60% | 4 | 4.4 | 1 | 2.18 | 5.46 | 0.87 | 7.87 |
| 41 | 141 | 70 | 1 | 5 | | | | 4 | | 6 | 65 | 4.9 | 1.80% | 5 | 4.9 | 1 | 2.46 | 6.15 | 1.42 | 8.42 |
| 42 | 125 | 70 | 1 | 72 | 1 | | | | | 0 | 72 | 3.8 | 1.40% | 4 | 3.8 | 1 | 1.9 | 4.75 | 0.3 | 7.3 |
| 43 | 95 | 70 | 1 | 76 | 1 | | | | | 0 | 76 | 3.7 | 1.40% | 4 | 3.7 | 1 | 1.85 | 4.63 | 0.2 | 7.2 |
| 44 | 80 | 70 | 1 | 39 | | 2 | | | | 1 | 78 | 3.9 | 1.50% | 4 | 3.9 | 1 | 1.97 | 4.93 | 0.44 | 7.44 |
| 45 | 66 | 70 | 1 | 5 | | | | 4 | | 7 | 75 | 4.7 | 1.80% | 5 | 4.7 | 0 | 0 | 0 | 1.22 | 8.22 |
| 46 | 40 | 70 | 1 | 5 | | | | 4 | | 8 | 85 | 4.6 | 1.70% | 5 | 4.6 | 0 | 0 | 0 | 1.11 | 8.11 |
| 47 | 13 | 70 | 1 | 7 | | | | 4 | | 7 | 105 | 4.2 | 1.50% | 4 | 4.2 | 1 | 2.08 | 5.2 | 0.66 | 7.66 |
| 48 | 9 | 70 | 1 | 106 | 1 | | | | | 0 | 106 | 2.8 | 1.00% | 3 | 2.8 | 1 | 1.41 | 3.53 | -0.67 | 6.33 |
| 49 | 6 | 70 | 1 | 110 | 1 | | | | | 0 | 110 | 2.7 | 1.00% | 3 | 2.7 | 1 | 1.33 | 3.33 | -0.83 | 6.17 |
| 50 | 1 | 70 | 1 | 133 | 1 | | | | | 0 | 133 | 2 | 0.70% | 2 | 2 | 1 | 0.99 | 2.47 | -1.53 | 5.47 |
| 51 | 28 | 70 | 0 | 8 | | 2 | | | | 8 | 72 | 4.1 | 1.50% | 4 | 4.1 | 1 | 2.05 | 5.13 | 0.6 | 7.6 |
| 52 | 19 | 70 | 0 | 8 | | 2 | | | | 8 | 72 | 3.9 | 1.50% | 4 | 3.9 | 0 | 0 | 0 | 0.44 | 7.44 |
| 53 | 10 | 70 | 0 | 8 | | 2 | | | | 2 | 24 | 2.7 | 1.00% | 3 | 2.7 | 0 | 0 | 0 | -0.8 | 6.2 |
| 54 | 7.83 | 70 | 0 | 144 | 1 | | | | | 0 | 144 | 2.9 | 1.10% | 3 | 2.9 | 1 | 1.45 | 3.62 | -0.6 | 6.4 |
| 55 | 6 | 70 | 0 | 144 | 1 | | | | | 0 | 144 | 2.8 | 1.00% | 3 | 2.8 | 1 | 1.39 | 3.48 | -0.72 | 6.28 |
| 56 | 5 | 70 | 0 | 144 | 1 | | | | | 0 | 144 | 2.7 | 1.00% | 3 | 2.7 | 0 | 0 | 0 | -0.8 | 6.2 |
| 57 | 6 | 70 | 0 | 144 | 1 | | | | | 0 | 144 | 2.8 | 1.00% | 3 | 2.8 | 1 | 1.39 | 3.48 | -0.72 | 6.28 |
| 58 | 7.83 | 70 | 0 | 144 | 1 | | | | | 0 | 144 | 2.9 | 1.10% | 3 | 2.9 | 1 | 1.45 | 3.62 | -0.6 | 6.4 |
| 59 | 8 | 70 | 0 | 4 | | | 3 | | | 8 | 36 | 3.3 | 1.20% | 3 | 3.3 | 0 | 0 | 0 | -0.24 | 6.76 |
| 60 | 17 | 70 | 0 | 4 | | | 3 | | | 8 | 36 | 3.6 | 1.30% | 4 | 3.6 | 1 | 1.79 | 4.48 | 0.09 | 7.09 |
| 61 | 26 | 70 | 0 | 4 | | | 3 | | | 2 | 12 | 2.8 | 1.00% | 3 | 2.8 | 1 | 1.41 | 3.52 | -0.68 | 6.32 |

FIG.7

SYSTEM AND METHOD FOR RELIEVING HYPERTENSION

CROSS-REFERENCE TO RELATED APPLICATIONS

This application claims foreign priority under 35 U.S.C. § 119(b) to Taiwanese Application Number 105121916, filed on Jul. 12, 2016.

BACKGROUND OF THE INVENTION

1. Fields of the Invention

The present invention relates to a system and method for relieving hypertension, and more particularly, to a technology for controlling and emitting electric energy waves to treat hypertension disease of animal or human.

2. Descriptions of Related Art

The type of hypertension can be divided into primary hypertension and spontaneous hypertension, of which about 90 to 95 percent of primary hypertension is the largest group of hypertensive population. The medical community believes that the causes of primary hypertension have a great relevance with genetic and living environment factors (such as diet of processed foods). Most processed foods are added a lot of salt to increase their flavor. People excessively intake sodium from those processed foods and result in getting chronic hypertension. Sodium is a mineral, an important and indispensable element for the human body. But the dietary intake with too much sodium will increase the body's blood pressure. Many medical studies have confirmed that dietary salt (such as sodium chloride) intake and blood pressure values have a significant correlation. Therefore, the medical profession generally has identified, excessive intake of salt is indeed the main cause of increased blood pressure in the human body. Of course, there are other factors (such as diabetes; or other diseases) also will resulting in high blood pressure.

So far, hypertension is considered to be one of the chronic diseases can't be completely cured, and therefore need to do drug control therapy. As long as the drug control used properly, the patient can get a satisfactory blood pressure control effect, i.e. under rational use of antihypertensive drugs, blood pressure can be maintained at normal or near normal levels, so as to alleviate discomfort, delay the progression of the disease, and prevent from cerebrovascular accident and other complications such as heart failure and renal failure.

Whether Western medicine or Chinese medicine treatment for hypertension, all belong to an invasive type of confrontation therapy. However, under long-term medication treatment, it will inevitably cause side effects of hurting liver and kidney. To solve this blind spot of medical technology, there are many related industries using resonant energy wave to treat and alleviate chronic diseases. While conventional resonant wave techniques have been known to introduce electrical energy waves into the human body to produce a resonance with the physiological frequency of the human body to achieve the alleviation effect for some particular diseases, however, for the treatment of chronic diseases of hypertension, the current known resonant energy wave technology or research, has not completely construct and develop a set of resonance frequency treatment formula for effectively relieve and improve symptom of high blood pressure of hypertension patient yet. Therefore, how to develop a set of resonant energy wave for effectively soothing and improving the symptom of high blood pressure hypertension patient has become an anxious problems and challenges for the industry to solve.

According to the theory of quantum medicine, all living things and life forms have their own physiological frequency (which is the biological resonant wave), and harmonized wave frequency occurs in healthy human bodies. On the other hand, a disordered wave frequency occurred in human body indicates functional degradation of the living thing and sickness caused by a harmonic interference of diseases or viruses. In 1930, American physicist, Royal Rife, discovered that every object contains bacteria and viruses having their own natural frequency, and such discovery was used by doctors of University of Southern California for medical tests in 1934 and satisfactory results were achieved. Royal Rife's research discovered that different resonant waves have different physiological reactions to human body. Thereafter, a Canadian corporation, Resonant Light Technology Inc. developed a resonant wave health instrument for measuring the physiological frequency of a human body. The electric energy wave emitted from the instrument has a wavelength of 4~20 microns (um), which is very close to the wavelength of the biological wave of a human body (3~45 um), so as to provide a healthcare function to human body. At present, researches on the subject of treating cancers by electromagnetic waves are conducted extensively. Although the prior art has introduced electric energy waves into human body to produce resonance with the physiological frequency of human body, so as to achieve the treatment effect, yet the conventional techniques or researches do not use the electric energy wave technology to create a frequency modulation treatment formulation for relieving hypertension effectively.

Since the biological resonant waves probably have high efficacy in curing human diseases, and the inventor of the present patent application has researched for a long time to apply the electric energy wave to reduce or eliminate high blood sugar factor of diabetes, the inventor of the present patent application has a first generation which had been issued for Taiwanese patent No. 1453046 and U.S. Pat. No. 9,421,368. After the aforementioned invention, the inventor of the present patent application puts into research applying such specific controls of energy wave to treat and improve hypertension disease of animal or human.

SUMMARY OF THE INVENTION

The primary objective of the present invention is to provide a system for relieving hypertension. The system comprises an energy wave generator including an energy wave's frequency control mode for controlling and generating energy waves. The energy wave's frequency control mode includes multiple controls in multiple energy wave generation periods respectively. The multiple controls act on the energy wave generator to generate and emit energy waves each with a corresponding energy density for effecting on bodies of animals or human for relieving hypertension. The energy density is calculated by a corresponding base frequency between 1~18150 Hz, a sweep bandwidth (Width) of the corresponding base frequency, an emission rate (D %) and a total time of emission (TT) in a duty cycle, so that the energy waves with the corresponding energy densities within values of 0.99~7.25 effect on the bodies of animals or human. The value of the energy density is calculated by the formula of ED=log 10 (base freq.×D %×(2Width+1)×(TT)+1).

BRIEF DESCRIPTION OF THE DRAWINGS

FIG. 7 is a schematic view of list of relations between spectrums of effect frequencies, modulation parameters and energy densities of one preferable embodiment of the present invention;

DETAILED DESCRIPTION OF THE PREFERRED EMBODIMENT

Figure 1:
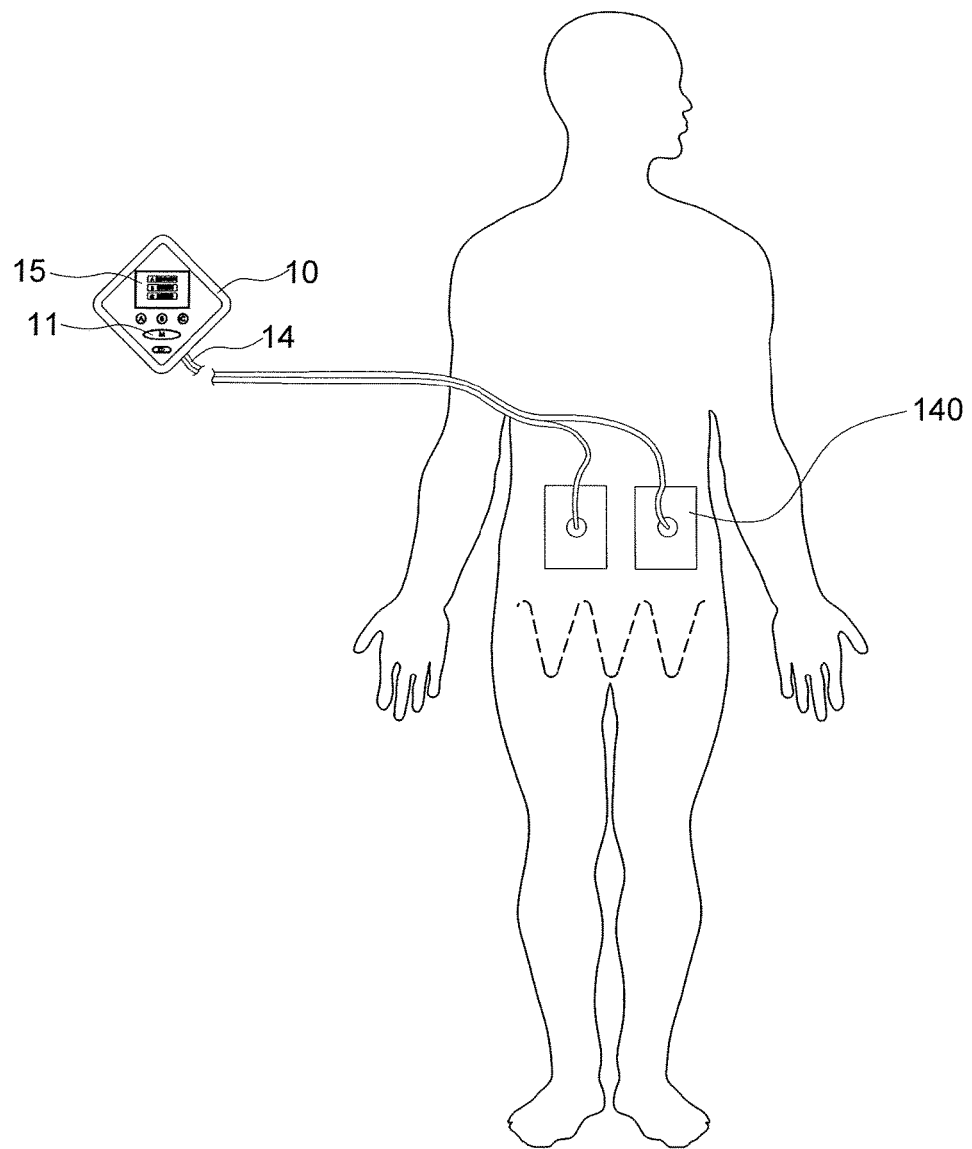
FIG. 1 is a schematic view of the system of the present invention.
Figure 2:
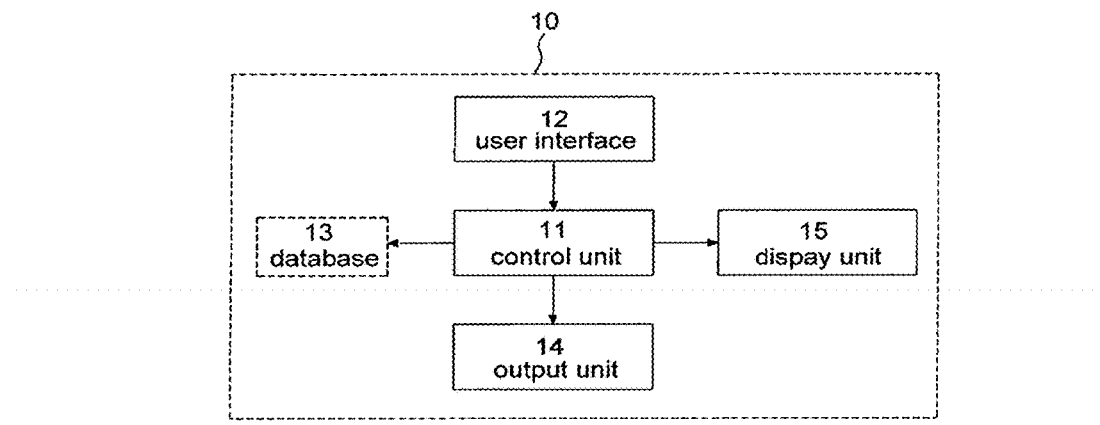
FIG. 2 is a schematic block diagram of units of the system of the present invention.

Referring to FIGS. 1 to 7, the system of the present invention comprises an energy wave generator 10. The energy wave generator 10 is set up with an energy wave's frequency control mode. The energy wave generator 10 generates and emits energy waves (i.e. resonant wave) according to the control of the energy wave's frequency control mode. In one embodiment, the energy wave's frequency control mode includes first to ninth sets of controls in corresponding first to ninth sets of energy wave generation periods. The energy wave generator 10 generates and emits the energy waves each with a corresponding energy density by a corresponding frequency sweep mode based on a corresponding base frequency in the first to ninth energy wave generation periods respectively according to the controls of the energy wave's frequency control mode, so that the energy waves effect on the body of animal or human to relieve their hypertension. Referring to FIGS. 1 to 2, the energy wave generator 10 comprises a user interface 12, a control unit 11, a database 13 for saving the information of spectrums of effect frequency and modulation parameters corresponding to each effect frequency used in each energy wave generation period, an energy wave output unit 14 and a display unit 15. In one embodiment of the present invention, the energy waves are in electric forms, and the energy wave output unit 14 includes a set of electrode sheets 140 for affixing to the body of animal or human so as to construct a circulation loop between the body and the electrical energy wave output unit 14 to transmit electric energy waves to the body of animal or human with hypertension. The control unit 11 (such as a combination of microcontroller and driving circuit) sequentially reads the information of spectrums and modulation parameters of effect frequencies in the database 13, and then drives the energy wave output unit 14 to sequentially generate and emit generates and emits electric energy waves each with a respective energy density (ED) in each corresponding energy wave generation period.

The control unit 11 of the present invention can be triggered to read the associated information of spectrums and modulation parameters in the database 13 by the command signals generated from the user interface 12, and then generates driving signals to control the energy wave output unit 14 (such as weak pulse generating circuit, voltage≤10V, current≤5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

Referring to FIG. 7, in one embodiment of the invention, the energy wave generator 10 according to the control of the energy wave's frequency control mode sequentially outputs the energy waves from first to ninth energy wave generation periods. The controls of the energy wave's frequency control mode are for: (a) continuously and sequentially generating a 1st to a 4th energy waves correspondingly with a 1st to a 4th energy densities by a 1st to a 4th base frequencies correspondingly in the first energy wave generation period, wherein, the 1st energy density of the 1st energy wave is between 2.47~6.19 (preferably 4.95), the 2nd energy density of the 2nd energy wave is between 2.51~6.28 (preferably 5.02), the 3rd energy density of the 3rd energy wave is between 2.49~6.24 (preferably 4.99), and the 4th energy density of the 4th energy wave is between 2.46~6.16 (preferably 4.92); (b) continuously and sequentially generating a 5th to a 11th energy waves correspondingly with a 5th to a 11th energy densities by a 5th to a 11th base frequencies correspondingly in the second energy wave generation period, wherein, the 5th energy density is between 2.52~6.29 (preferably 5.03), the 6th energy density between 2.36~5.89 (preferably 4.71), the 7th energy density is between 2.90~7.25 (preferably 5.80), the 8th energy density is between 2.34~5.85 (preferably 4.68), the 9th energy density is between 2.34~5.85 (preferably 4.68), the 10th energy density is between 2.31~5.78 (preferably 4.63), the 11th energy density is between 2.28~5.70 (preferably 4.56); (c) continuously and sequentially generating a 12th to a 17th energy waves correspondingly with a 12th to a 17th energy densities by a 12th to a 17th base frequencies correspondingly in the third energy wave generation period, wherein, the 12th energy density is between 2.23~5.58 (preferably 4.46), the 13th energy density is between 2.37~5.93 (preferably 4.75), the 14th energy density is between 2.79~6.98 (preferably 5.58), the 15th energy density is between 2.89~7.21 (preferably 5.77), the 16th energy density is between 2.21~5.51 (preferably 4.41), the 17th energy density is between 2.77~6.92 (preferably 5.54); (d) continuously and sequentially generating a 18th to a 23rd energy waves correspondingly with a 18th to a 23rd energy densities by a 18th to a 23rd base frequencies correspondingly in the fourth energy wave generation period, wherein, the 18th energy density is between 2.17~5.42 (preferably 4.34), the 19th energy density is between 2.57~6.41 (preferably 5.13), the 20th energy density is between 2.81~7.02 (preferably 5.61), the 21st energy density is between 2.14~5.36 (preferably 4.29), the 22nd energy density is between 2.48~6.21 (preferably 4.97), the 23rd energy density is between 2.43~6.07 (preferably 4.86); (e) continuously and sequentially generating a 24th to a 28th energy waves correspondingly with a 24th to a 28th energy densities by a 24th to a 28th base frequencies correspondingly in the fifth energy wave generation period, wherein, the 24th energy density is between 2.29~5.73 (preferably 4.58), the 25th energy density is between 2.18~5.46 (preferably 4.37), the 26th the energy density is between 2.46~6.15 (preferably 4.92), the 27th energy density is between 1.90~4.75 (preferably 3.80), the 28th energy density is between 1.85~4.63 (preferably 3.70); (f) continuously and sequentially generating a 29th to a 33rd energy waves correspondingly with a 29th to a 33rd energy densities by a 29th to a 33rd base frequencies correspondingly in the sixth energy wave generation period, wherein, the 29th energy density is between 2.08~5.20 (preferably 4.16), the 30th energy density is between 1.41~3.53 (preferably 2.83), the 31st energy density is between 1.33~3.33 (preferably 2.67), the 32nd energy density is between 0.99~2.47 (preferably 1.97), the 33rd energy density is between 2.05~5.13 (preferably 4.10); (g) continuously and sequentially generating a 34th to a 35th energy waves correspondingly with a 34th to a 35th energy densities by a 34th to a 35th base frequencies correspondingly in the seventh energy wave generation period, wherein, the 34th energy density is between 1.45~3.62 (preferably 2.90), the 35th energy density is between 1.39~3.48 (preferably 2.78); (h) continuously and sequentially generating a 36th to a 37th energy waves correspondingly with a 36th to a 37th energy densities by a 36th to a 37th base frequencies correspondingly in the eighth energy wave generation period, wherein, the 36th energy density is between 1.39~3.48 (preferably 2.78), the 37th energy density is between 1.45~3.62 (preferably 2.90); and (i) continuously and sequentially generating a 38th to a 39th energy waves correspondingly with a 38th to a 39th energy densities by a 38th to a 39th base frequencies correspondingly in the ninth energy wave generation period, wherein, the 38th energy density is between 1.79~4.48 (preferably 3.59), and the 39th energy density is between 1.41~3.52 (preferably 2.82).

The value of aforementioned energy densities of the energy waves by their corresponding frequencies are calculated by the formula: ED=log 10 (base freq.×D %×(2Width+1)×(TT)+1). For example of the 1st base frequency in the first energy wave generation period, if we set the 1st base freq.=18122 Hz, the emission rate in a duty cycle (D %)=70%, the sweep bandwidth (Width) (m)=0 Hz and the total time of emission (TT)=7 secs in a duty cycle, and then the energy density (ED)=log 10 (18122×70%×(2×0+1)×7+1)=4.95. Although there is no specific unit referring to the energy density (ED) of the present invention, the ED has real meaning, which represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy density exceeds the scope of the set ones, the efficiency also will be changed with it.

Figure 3:
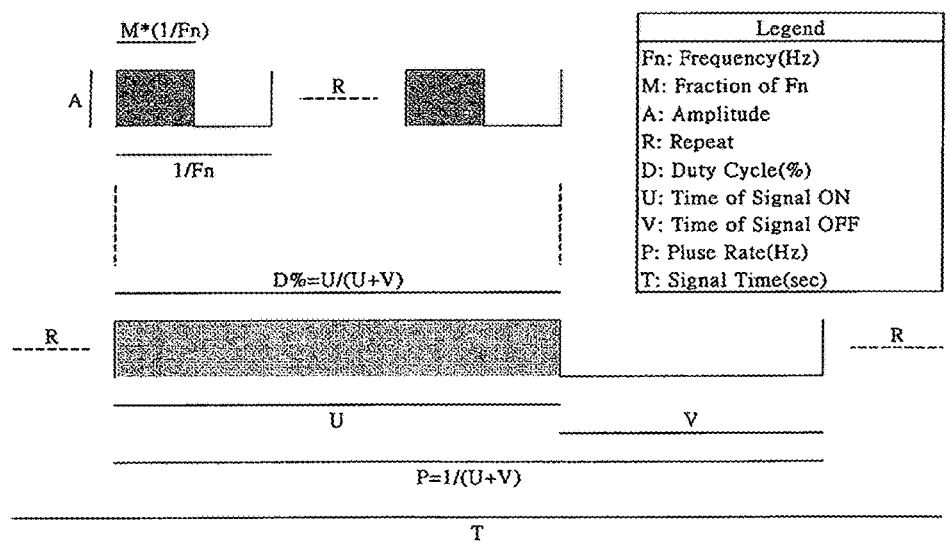
FIG. 3 is a schematic view of wave form of a duty cycle of the present invention.

As shown in FIGS. 3 and 7, in one embodiment of the present invention, the energy wave is a square wave, D is the duty cycle, T is effect time of a single frequency, D % is emission rate of duty cycle of each base frequency and equal to U/(U+V). In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pluse Rate (Hz) of frequency, P=1/(U+V). TT is the total time of emission period based on each base frequency in each duty cycle. In FIG. 7, the normalized percentages (normal) in each order, is the ratio between the ED in the effect period based on each base frequency and the sum of ED of the whole effect periods based on whole base frequencies from order 1 to 61 shown in FIG. 7.

Referring to FIG. 7, during the first energy wave generation period, the control mode of the 1st frequency is fixed frequency sweep mode, which sets a fixed 1st base frequency within 18100~18150 Hz (preferably 18122 Hz), emission rate (D %)=70% for a duty cycle, sweep bandwidth (Width) (m)=0 Hz and total time of emission (TT)=7 seconds for a duty cycle; the control mode of the 2nd frequency is fixed frequency sweep mode, which sets a fixed 2nd base frequency within 9900~10100 Hz (preferably 10000 Hz), D %=70%, Width (m)=0 Hz and TT=15 secs for a duty cycle; the control mode of the 3rd frequency is fixed frequency sweep mode, which sets a fixed 3rd base frequency within 7300~7400 Hz (preferably 7344 Hz), D %=70%, Width (m)=0 Hz and TT=19 secs for a duty cycle; and the control mode of the 4th frequency is fixed frequency sweep mode, which sets a fixed 4th base frequency within 4980~5020 Hz (preferably 5000 Hz), D %=70%, Width (m)=0 Hz and TT=24 secs for a duty cycle.

Referring to FIG. 7, during the second energy wave generation period, the control mode of the 5th frequency is a sweep decreasing mode, which sets effect frequencies decreasingly adjusted based on a 5th base frequency between 2100~2150 Hz (preferably 2127 Hz) with D %=70%, Width=1 Hz, adjusted bandwidth equal to 1 Hz, and TT=36 secs for a duty cycle; the control mode of the 6th frequency is a fixed frequency sweep mode, which sets a fixed 6th base frequency between 2100~2130 Hz (preferably 2112 Hz) with D %=70%, Width (m)=0 Hz and TT=35 secs for a duty cycle. The control mode of the 7th frequency is a spread contract mode, which sets effect frequencies decreasing and increasing alternately adjusted to contract based on a 7th base frequency between 1950~2030 Hz (preferably 2007 Hz) with D %=70%, Width=7 Hz, adjusted bandwidth equal to 1 Hz and TT=30 seconds; the control mode of the 8th frequency is a fixed frequency sweep mode, which sets a fixed 8th base frequency between 1860 Hz~1880 Hz (preferably 1865 Hz) with D %=70%, Width (m)=0 Hz and TT=37 secs for a duty cycle; the control mode of the 9th base frequency is a fixed frequency sweep mode, which sets a fixed 9th base frequency between 1845 Hz~1855 Hz (preferably 1850 Hz) with D %=70%, Width (m)=0 Hz and TT=37 secs for a duty cycle; the control mode of the 10th frequency is a fixed frequency sweep mode, which sets a fixed 10th base frequency between 1530~1570 Hz (preferably 1550 Hz) with D %=70%, Width (m)=0 Hz and TT=39 secs for a duty cycle; and the control mode of the 11th frequency is a fixed frequency sweep mode, which sets a fixed 11th base frequency between 1220~1250 Hz (preferably 1234 Hz) with D %=70%, Width (m)=0 Hz and TT=42 secs for a duty cycle.

Referring to FIG. 7, during the third energy wave generation period, the control mode of the 12th frequency is a fixed frequency sweep mode, which sets a fixed 12th base frequency between 870 Hz~890 Hz (preferably 880 Hz) with D %=70%, Width (m)=0 Hz and TT=47 secs for a duty cycle; the control mode of the 13th frequency is a sweep decreasing mode, which sets effect frequencies decreasingly adjusted based on a 13th base frequency between 860~880 Hz (preferably 867 Hz) with D %=70%, Width=1 Hz, adjusted bandwidth equal to 1 Hz, and TT=46 seconds for a duty cycle; the control mode of the 14th frequency is a spread contract mode, effect frequencies decreasing and increasing alternately adjusted to contract based on a 14th base frequency between 800 Hz~820 Hz (preferably 807 Hz) with D %=70%, Width (m)=7 Hz, adjusted bandwidth=1 Hz and TT=45 secs for a duty cycle; the control mode of the 15th frequency is a spread contract mode, which sets effect frequencies decreasing and increasing alternately adjusted to contract based on a 15th base frequency between 770 Hz~785 Hz (preferably 778 Hz) with D %=70%, Width (m)=9 Hz, adjusted bandwidth=1 Hz and TT=57 secs for a duty cycle; the control mode of the 16th frequency is a fixed frequency sweep mode, which sets a fixed 16th base frequency between 745 Hz~765 Hz (preferably 751 Hz) with D %=70%, Width (m)=0 Hz and TT=49 secs for a duty cycle; and the control mode of the 17th frequency is a spread contract mode, which sets effect frequencies decreasing and increasing alternately adjusted to contract based on a 17th base frequency between 720 Hz~740 Hz (preferably 730 Hz) with D %=70%, Width (m)=7 Hz, adjusted bandwidth=1 Hz and TT=45 secs for a duty cycle.

Referring to FIG. 7, during the fourth energy wave generation period, the control mode of the 18th frequency is a fixed frequency sweep mode, which sets a fixed 18th base frequency between 605 Hz~620 Hz (preferably 612 Hz) with D %=70%, Width (m)=0 Hz and TT=51 secs for a duty cycle; the control mode of the 19th frequency is a sweep increasing mode, which sets effect frequencies increasingly adjusted based on a 19th base frequency between 590~610 Hz (preferably 595 Hz) with D %=70%, Width (m)=5 Hz, adjusted bandwidth=1 Hz and TT=54 secs for a duty cycle; the control mode of the 20th frequency is a spread contract mode, which sets effect frequencies decreasing and increasing alternately adjusted to contract based on a 20th base frequency between 535~560 Hz (preferably 542 Hz) with D %=70%, Width (m)=9 Hz, adjusted bandwidth=1 Hz and TT=57 secs for a duty cycle; the control mode of the 21st frequency is a fixed frequency sweep mode, which sets a fixed 21st base frequency between 515~535 Hz (preferably 522 Hz) with D %=70%, Width (m)=0 Hz and TT=53 secs for a duty cycle; the control mode of the 22nd frequency is a sweep increasing mode, which sets effect frequencies increasingly adjusted based on a 22nd base frequency between 480~495 Hz (preferably 484 Hz) with D %=70%, Width (m)=4 Hz, adjusted bandwidth=1 Hz and TT=55 secs for a duty cycle; the control mode of the 23rd frequency is a sweep decreasing mode, which sets effect frequencies decreasingly adjusted based on a 23rd base frequency between 455~475 Hz (preferably 462 Hz) with D %=70%, Width (m)=3 Hz, adjusted bandwidth=1 Hz and TT=56 secs for a duty cycle.

Referring to FIG. 7, during the fifth energy wave generation period, the control mode of the 24th frequency is a sweep decreasing mode, which sets effect frequencies decreasingly adjusted based on a 24th base frequency between 295~310 Hz (preferably 302 Hz) with D %=70%, Width (m)=2 Hz, adjusted bandwidth=1 Hz and TT=60 secs for a duty cycle; the control mode of the 25th frequency is a sweep increasing mode, which sets effect frequencies increasingly adjusted based on a 25th base frequency between 155~170 Hz (preferably 160 Hz) with D %=70%, Width (m)=2 Hz, adjusted bandwidth=1 Hz and TT=69 secs for a duty cycle; the control mode of the 26th frequency is a spread contract mode, which sets effect frequencies decreasing and increasing alternately adjusted to contract based on a 26th base frequency between 135~150 Hz (preferably 141 Hz) with D %=70%, Width (m)=6 Hz, adjusted bandwidth=1 Hz and TT=65 secs for a duty cycle; the control mode of the 27th frequency is a fixed frequency sweep mode, which sets a fixed 27th base frequency between 120~135 Hz (preferably 125 Hz) with D %=70%, Width (m)=0 Hz and TT=72 secs for a duty cycle; and the control mode of the 28th frequency is a fixed frequency sweep mode, which sets a fixed 28th base frequency between 90~110 Hz (preferably 95 Hz) with D %=70%, Width (m)=0 Hz and TT=76 secs for a duty cycle.

Referring to FIG. 7, during the sixth energy wave generation period, the control mode of the 29th frequency is a spread contract mode, which sets effect frequencies decreasing and increasing alternately adjusted to contract based on a 29th base frequency between 10~20 Hz (preferably 13 Hz) with D %=70%, Width (m)=7 Hz, adjusted bandwidth=1 Hz and TT=105 secs for a duty cycle; the control mode of the 30th frequency is a fixed frequency sweep mode, which sets a fixed 30th base frequency between 5~25 Hz (preferably 9 Hz) with D %=70%, Width (m)=0 Hz and TT=106 secs for a duty cycle; the control mode of the 31st frequency is a fixed frequency sweep mode, which sets a fixed 31st base frequency between 4~15 Hz (preferably 6 Hz) with D %=70%, Width (m)=0 Hz and TT=110 secs for a duty cycle; the control mode of the 32nd frequency is a fixed frequency sweep mode, which sets a fixed 32nd base frequency between 1~6 Hz (preferably 1 Hz) with D %=70%, Width (m)=0 Hz and TT=133 secs for a duty cycle; and the control mode of the 33rd frequency is a sweep decreasing mode, which sets effect frequencies decreasingly adjusted based on a 33rd base frequency between 25~45 Hz (preferably 28 Hz) with D %=70%, Width (m)=8 Hz, adjusted bandwidth=1 Hz and TT=72 secs for a duty cycle.

Referring to FIG. 7, during the seventh energy wave generation period, the control mode of the 34th frequency is a fixed frequency sweep mode, which sets a fixed 34th base frequency between 5~20 Hz (preferably 7.83 Hz) with D %=70%, Width (m)=0 Hz and TT=144 secs for a duty cycle; and the control mode of the 35th frequency is a fixed frequency sweep mode, which sets a fixed 35th base frequency between 5~15 Hz (preferably 6 Hz) with D %=70%, Width (m)=0 Hz and TT=144 secs for a duty cycle.

Referring to FIG. 7, during the eighth energy wave generation period, the control mode of the 36th frequency is a fixed frequency sweep mode, which sets a fixed 36th base frequency between 5~8 Hz (preferably 6 Hz) with D %=70%, Width (m)=0 Hz and TT=144 secs for a duty cycle; and the control mode of the 37th frequency is a fixed frequency sweep mode, which sets a fixed 37th base frequency between 6~15 Hz (preferably 7.83 Hz) with D %=70%, Width (m)=0 Hz and TT=144 secs for a duty cycle.

Referring to FIG. 7, during the ninth energy wave generation period, the control mode of the 38th frequency is a sweep increasing mode, which sets effect frequencies increasingly adjusted based on a 38th base frequency between 15~28 Hz (preferably 17 Hz) with D %=70%, Width (m)=8 Hz, adjusted bandwidth=1 Hz and TT=36 secs for a duty cycle; and the control mode of the 39th frequency is a sweep increasing mode, which sets effect frequencies increasingly adjusted based on a 39th base frequency between 24~35 Hz (preferably 26 Hz) with D %=70%, Width (m)=2 Hz, adjusted bandwidth=1 Hz and TT=12 secs for a duty cycle.

The fixed frequency sweep mode depicted in the present invention means the frequency of each treatment functioning at a fixed frequency until the total time of the frequency effect period ends. In the case of the first energy wave generation period, for example, assuming that the first frequency is 18122 Hz, then the first frequency is fixed at 18122 Hz until the total time of the frequency reaches 7 seconds. After that, it goes to the next frequency effect period, and so on. Because there is no value change of the frequency range for the fixed frequency sweep mode, therefore, the sweep bandwidth is 0 Hz.

Figure 4:
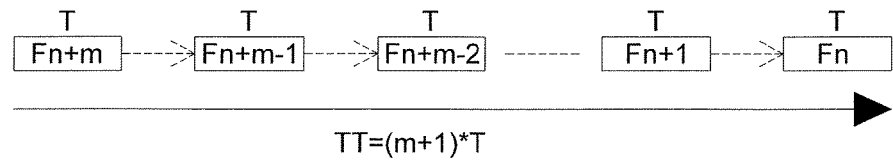
FIG. 4 is a schematic view of distribution of effect frequencies calculated by the sweep decreasing mode of the present invention.

Referring to FIGS. 4 and 7, the control of the aforementioned sweep decreasing mode is to control the system to emit the energy wave by frequency decreasing distribution with an adjusted bandwidth in a predetermined bandwidth. The calculation of the value change of the sweep decreasing mode depicted in the present invention is described as below. The first output frequency is calculated as a base frequency (Fn) plus a sweep bandwidth (m), and the second output frequency is calculated as the first output frequency minus an adjusted bandwidth (such as 1 Hz). When the current output frequency is equal to the base frequency (Fn), the current output frequency will be the last output frequency. In the case of the 5th frequency, for example, the base frequency is 2127 Hz with Width=1 Hz. Based on the above formula, two frequencies can be obtained, and the sequence of the output frequency is 2128 Hz and 2127 Hz respectively. Each single-frequency's effect time (T) in the sweep decreasing mode is 18 seconds, so the total time of the two frequencies (TT) is 36 seconds, i.e., TT=(m+1)*T.

Figure 5:
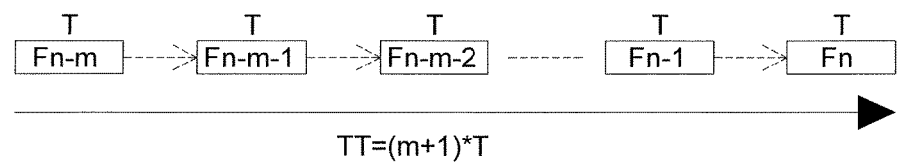
FIG. 5 is a schematic view of distribution of effect frequencies calculated by the sweep increasing mode of the present invention.

Referring to FIGS. 5 and 7, the control of the aforementioned sweep increasing mode is to control the system to emit the energy wave by frequency increasing distribution with an adjusted bandwidth in a predetermined sweep bandwidth. The calculation of the value change of the sweep increasing mode depicted in the present invention is described as below. The first output frequency is calculated as a base frequency (Fn) minus a sweep bandwidth (m), and the second output frequency is calculated as the first output frequency plus an adjusted bandwidth (such as 1 Hz). When the current output frequency is equal to the base frequency (Fn), the current output frequency will be the last output frequency. In the case of the 19th frequency, for example, the base frequency is 595 Hz with sweep bandwidth (Width) 5 Hz and adjusted bandwidth 1 Hz. Based on the above formula, six frequencies can be obtained, and the sequence of the output frequency is 590 Hz, 591 Hz, 592 Hz, 593 Hz, 594 Hz and 595 Hz respectively. Each single-frequency's effect time (T) in the sweep increasing mode is 9 seconds, so that the total time of the six frequencies (TT) is 54 seconds, i.e., TT=(m+1)*T.

Figure 6:
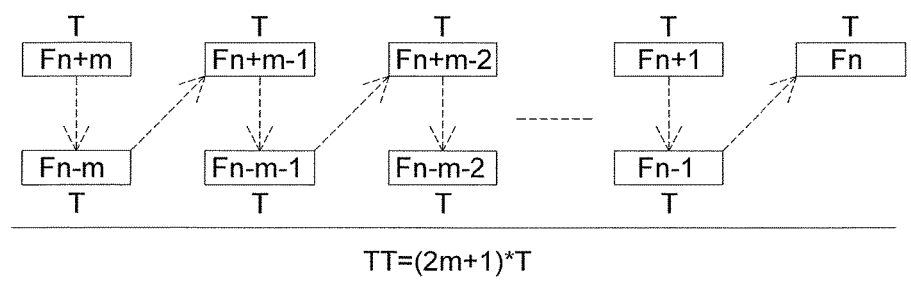
FIG. 6 is a schematic view of distribution of effect frequencies calculated by the spread contract mode of the present invention.

Referring to FIGS. 6 and 7, the control of the aforementioned spread contract mode is to control the system to emit the energy wave by alternating increasing frequency and decreasing frequency distribution with an adjusted bandwidth in a predetermined bandwidth. The calculation of the value change of the spread contract mode depicted in the present invention is described as below. The first output frequency is calculated as a base frequency (Fn) minus a sweep bandwidth (m), the second output frequency is calculated as a base frequency (Fn) plus a sweep bandwidth (m), the third output frequency is calculated as the first output frequency plus an adjusted bandwidth (such as 1 Hz), the fourth output frequency is calculated as the second output frequency minus an adjusted bandwidth (such as 1 Hz), and so on. When the current output frequency is equal to the base frequency (Fn), the current output frequency will be the last output frequency. In the case of the 7th frequency, for example, the base frequency is 2007 Hz with sweep bandwidth (m) 7 Hz and adjusted bandwidth 1 Hz. Based on the above formula, fifteen frequencies can be obtained, and the sequence of the output frequency is 2000 Hz, 2014 Hz, 2001 Hz, 2013 Hz, 2002 Hz, 2012 Hz, 2003 Hz, 2011 Hz, 2004 Hz, 2010 Hz, 2005 Hz, 2009 Hz, 2006 Hz, 2008 Hz and 2007 Hz respectively. Each single-frequency's treatment time (T) is 2 seconds, so that the total time of the fifteen frequencies (TT) is 30 seconds, i.e., TT=(2 m+1)*T.

On the chart shown in FIG. 7, the frequency distributions of first to ninth energy wave generation periods are from orders 1-4, 9-15, 19-24, 29-34, 39-43, 47-51, 54-55, 57-58 and 60-61 chronologically respectively.

In one preferable embodiment of the present invention, according to the energy wave's frequency control mode, the energy wave generator 10 sequentially outputs a 1st and a 2nd subsequent energy waves correspondingly with a 1st and a 2nd subsequent energy densities by 1st and a 2nd subsequent base frequencies correspondingly after the 4th energy wave in the first energy wave generation period, outputs a 3rd subsequent energy wave with a corresponding 3rd subsequent energy density by a corresponding 3rd subsequent base frequency after the 11th energy wave in the second energy wave generation period, outputs a 4th subsequent energy wave with a corresponding 4th subsequent energy density by a corresponding 4th subsequent base frequency after the 17th energy wave in the third energy wave generation period, outputs a 5th subsequent energy wave with a corresponding 5th subsequent energy density by a corresponding 5th subsequent base frequency after the 23th energy wave in the fourth energy wave generation period, and outputs a 6th subsequent energy wave with a corresponding 6th subsequent energy density by a corresponding 6th subsequent base frequency after the 28th energy wave in the fifth energy wave generation period. Wherein, the 1st subsequent energy density is between 2.44~6.10 (preferably 4.88), the 2nd subsequent energy density is between 2.43~6.07 (preferably 4.86), the 3rd subsequent energy density is between 2.255.63 (preferably 4.51), the 4th subsequent energy density is between 2.49~6.22 (preferably 4.98), the 5th subsequent energy density is between 2.63~6.58 (preferably 5.26), and the 6th subsequent energy density is between 1.97~4.93 (preferably 3.94).

The control mode of the 1st subsequent base frequency is a fixed frequency sweep mode, which sets a fixed 1st subsequent base frequency between 4100~4300 Hz (preferably 4200 Hz) with D %=70%, Width (m)=0 Hz and TT=26 secs for a duty cycle. The control mode of the 2nd subsequent base frequency is a fixed frequency sweep mode, which sets a fixed 2nd subsequent base frequency between 3600~4090 Hz (preferably 3672 Hz) with D %=70%, Width (m)=0 Hz and TT=28 secs for a duty cycle. The control mode of the 3rd subsequent base frequency is a fixed frequency sweep mode, which sets a fixed 3rd subsequent base frequency between 1000~1100 Hz (preferably 1043 Hz) with D %=70%, Width (m)=0 Hz and TT=44 secs for a duty cycle. The control mode of the 4th subsequent base frequency is a sweep decreasing mode, which sets effect frequencies decreasingly adjusted based on a 4th subsequent base frequency between 680~720 Hz (preferably 705 Hz) with D %=70%, Width=3 Hz, adjusted bandwidth equal to 1 Hz, and TT=48 seconds for a duty cycle. The control mode of the 5th subsequent base frequency is a sweep increasing mode, which sets effect frequencies increasingly adjusted based on a 5th subsequent base frequency between 400~450 Hz (preferably 435 Hz) with D %=70%, Width (m)=9 Hz, adjusted bandwidth=1 Hz and TT=60 secs for a duty cycle. The control mode of the 6th subsequent base frequency is a sweep decreasing mode, which sets effect frequencies decreasingly adjusted based on a 6th subsequent base frequency between 60~95 Hz (preferably 80 Hz) with D %=70%, Width=1 Hz, adjusted bandwidth equal to 1 Hz, and TT=78 seconds for a duty cycle.

On the chart shown in FIG. 7, the frequency distributions of the 1st to 6th subsequent base frequencies are orders 5-6, 16, 25, 35 and 44 chronologically respectively.

Figure 8:
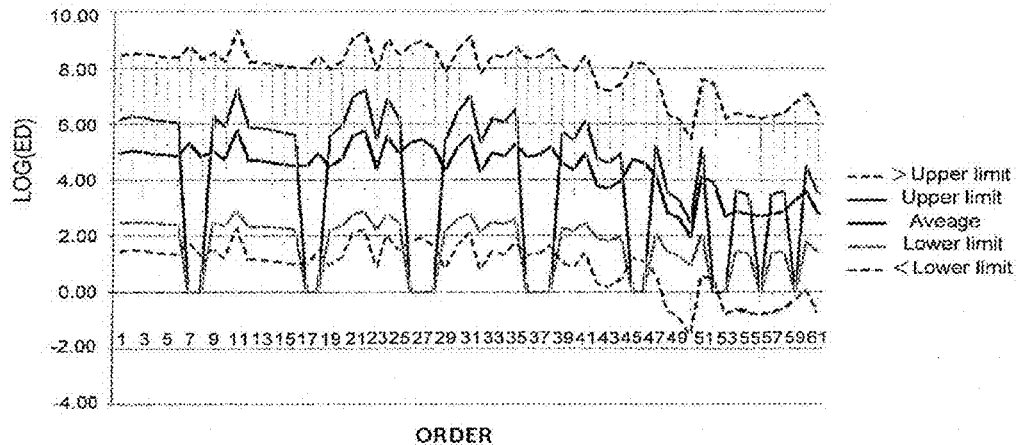
FIG. 8 is a schematic view of distribution of energy density on linear timeline of the present invention.
Figure 9:
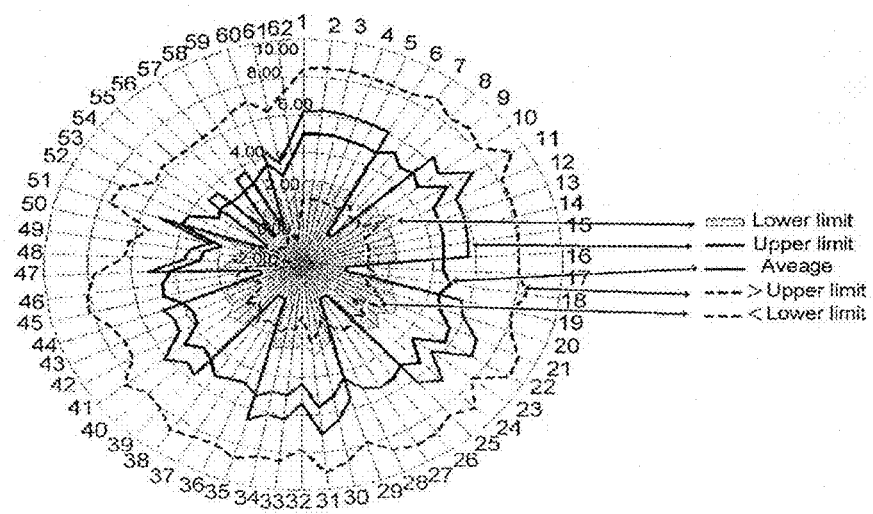
FIG. 9 is a schematic view of distribution of energy density on circular timeline of the present invention.

FIG. 8 shows the distribution schematic of the energy density in energy wave's frequency control mode against the linear timeline in the present invention. Wherein, the upper limit and the lower limit shown in FIG. 7 represent the upper range and the lower range of the energy density against the timeline mentioned above in accordance with the present invention. FIG. 9 shows the distribution schematic of the energy density in energy wave's frequency control mode against the annular timeline in the present invention. Wherein, the central portion is the average distribution of the energy density against the timeline mentioned above in accordance with the present invention.

In the present embodiment, besides above frequency treatment period, the energy wave's frequency control mode also includes eight non-energy periods, i.e., from the first to the eighth non-energy periods are generated between every two adjacent periods from the first to the ninth periods correspondingly. The total times of the first to eighth non-energy periods are 61, 90, 163, 171, 160, 96, 144 and 36 seconds respectively. The energy wave generator 10 generates various base frequencies in each non-energy period and filters the energy density of the various base frequencies to zero. Referring to FIG. 7, the first to the eighth non-energy periods are chronologically generated in-between order 7-8, order 17-18, order 26-28, order 36-38, order 45-46, order 52-53, order 56 and order 59 in sequence.

Figure 10:
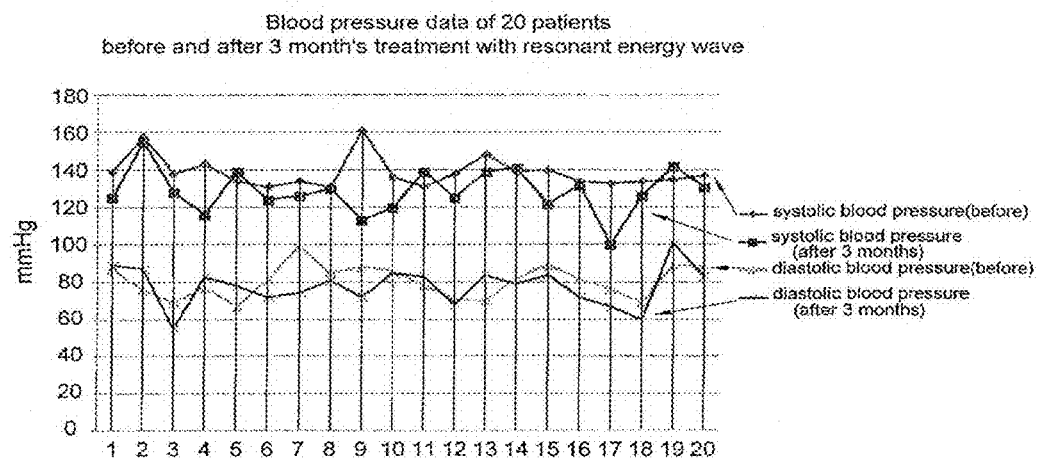
FIG. 10 is a schematic view of experimental comparisons of blood pressure values between before and after treatment of resonant energy wave of the present invention.
Figure 11:
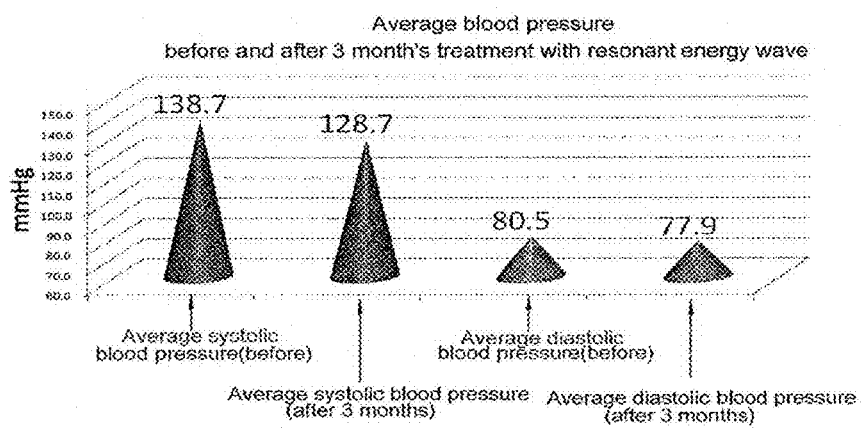
FIG. 11 is a schematic view of experimental average values of blood pressure after treatment of resonant energy wave for three month of the present invention.
Figure 12:
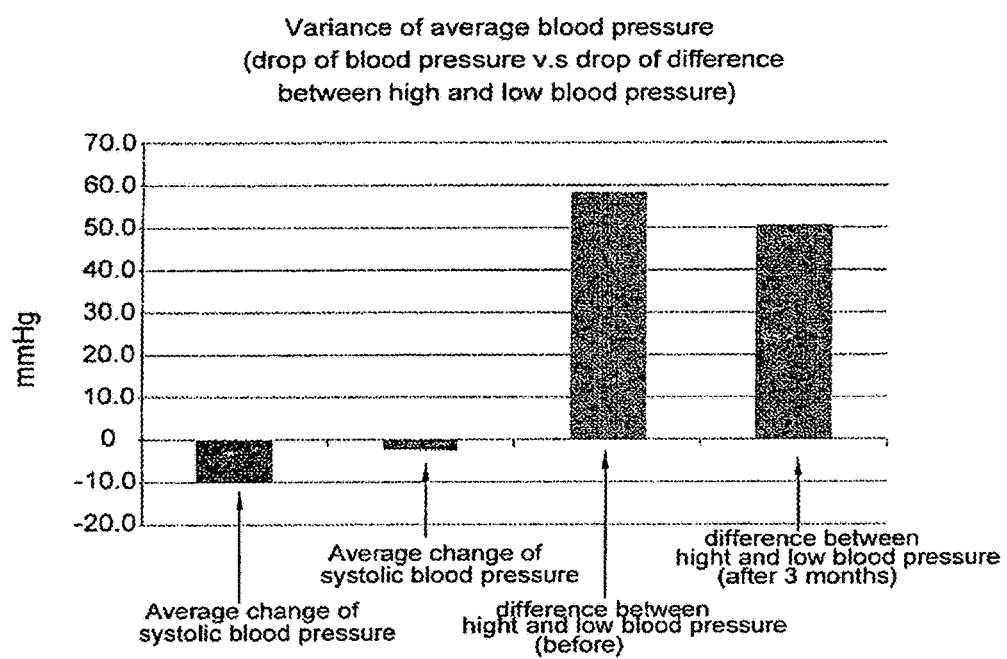
FIG. 12 is a schematic view of experimental comparisons of difference of blood pressure levels between before and after treatment of resonant energy wave of the present invention.

Referring to FIGS. 10 to 12, in order to verify the feasibility of the present invention, the inventor has carried out clinical experiments by 20 patients with hypertension treated with resonant energy wave of the present invention. FIG. 10 shows that there is significant decline in high blood pressure between before and after three month's treatment with resonant energy wave. Comparison in FIG. 11, before treatment of resonant energy wave, the average systolic blood pressure is 138.7 mmHg and the average diastolic blood pressure is 80.5 mmHg; and after treatment of resonant energy wave for three months, the average systolic blood pressure is 128.7 mmHg and the average diastolic blood pressure is 77.9 mmHg. As shown in FIG. 12, the average change value in systolic blood pressure is −10.1 mmHg and the average change value in diastolic blood pressure is −2.6 mmHg; before treatment with resonant energy wave, the difference between the high and low pressure is 58.3 mmHg, and after three month's treatment with resonant energy wave, the difference between high and low blood pressure is decreased to 50.8 mmHg. It can be seen that the present invention does have some degree of soothing and improved efficacy for hypertensive patients. In addition, it must be noted that blood pressure in the medical field will also refer to the reduction of difference between high and low blood pressure (that is difference between systolic blood pressure and diastolic blood pressure), because greater difference between high and low blood pressure results in higher risk of cardiovascular diseases.

While we have shown and described the embodiment in accordance with the present invention, it should be clear to those skilled in the art that further embodiments may be made without departing from the scope of the present invention.

What is claimed is:

1. A system for relieving hypertension, comprising an energy wave generator, the energy wave generator including a user interface, a control unit including an energy wave's frequency control mode, and an energy wave output unit with a set of electrode sheets for affixing to a body of animal or human so as to construct a circulation loop between the body and the energy wave output unit; the energy wave's frequency control mode including multiple controls in multiple energy wave generation periods respectively, the multiple controls acting on the energy wave generator to generate and emit energy waves each with a corresponding energy density in the multiple energy wave generation periods, the energy density of each energy wave being calculated by a corresponding base frequency between 1~18150 Hz, a sweep bandwidth (Width) of the corresponding base frequency, an emission rate (D %) and a total time of emission (TT) in a duty cycle, so that the energy waves with the corresponding energy densities within values of 0.99~7.25 effecting on the body of animal or human to relieve hypertension, the value of the energy density of each energy wave based on the corresponding base frequency being calculated by the formula of ED=log 10 (base freq.×D %×(2 Width+1)×(TT)+1).

2. The system as claimed in claim 1, wherein there is at least one non-energy period between every two adjacent periods of the multiple energy wave generation periods, the energy wave generator generates at least one base frequency in each non-energy period and filters at least one energy density of the at least one base frequency to zero.

3. The system as claimed in claim 1, wherein the multiple controls act on the energy wave generator in the multiple energy wave generation periods to sequentially output multiple sets of energy waves with corresponding multiple sets of energy densities between 2.46~6.28 and 1.41~4.48.

4. The system as claimed in claim 3, wherein the D %=70%, the Width is 0, 2 or 8 Hz, and the TT=7, 12, 15, 19, 24, or 36 secs; the base frequencies are between 18100~18150 Hz, 9900~10100 Hz, 7300~7400 Hz, 4980~5020 Hz or 24~35 Hz.

5. The system as claimed in claim 1, wherein the multiple controls act on the energy wave generator in the multiple energy wave generation periods to sequentially output multiple sets of energy waves with corresponding multiple sets of energy densities between 2.46~6.28, 2.21~7.21, 1.85~6.15, 1.39~3.62 and 1.41~4.48.

6. The system as claimed in claim 5, wherein the D %=70%, the Width is 0, 1, 2, 6, 7, 8 or 9 Hz, and the TT=7, 12, 15, 19, 24, 36, 45, 46, 47, 49, 57, 60, 65, 69, 72, 76 or 144 secs; the base frequencies are between 18100~18150 Hz, 9900~10100 Hz, 7300~7400 Hz, 4980~5020 Hz, 870~890 Hz, 860~880 Hz, 800~820 Hz, 770~785 Hz, 745~765 Hz, 720~740 Hz, 295~310 Hz, 155~170 Hz, 135~150 Hz, 120~135 Hz, 90~110 Hz, 5~20 Hz, 5~15 Hz, 15~28 Hz or 24~35 Hz.

7. The system as claimed in claim 1, wherein the multiple controls are nine sets, the multiple energy wave generation periods are nine sequentially from a 1st to a 9th corresponding to the nine sets of controls from a 1st to a 9th, the nine sets of controls act on the energy wave generator to sequentially output nine sets of energy waves from a 1st to a 9th with corresponding nine sets of energy densities between 2.46~6.28, 2.28~7.25, 2.21~7.21, 2.14~7.02, 1.85~6.15, 0.99~5.20, 1.39~3.62, 1.39~3.62 and 1.41~4.48.

8. The system as claimed in claim 7, wherein there are eight non-energy periods from a first 1st to an 8th non-energy period sequentially between every two adjacent periods of the multiple energy wave generation periods, the energy wave generator generates various base frequencies in each non-energy period and filters energy densities of the various base frequencies to zero.

9. The system as claimed in claim 8, wherein the total times of the 1st to 8th non-energy periods are 115, 134, 211, 231, 238, 96, 144 and 36 seconds respectively.

10. The system as claimed in claim 7, wherein in the 1st energy wave generation period corresponding to the 1st set of controls, the 1st set of energy waves are sequentially a 1st to a 4th energy waves correspondingly with a 1st to a 4th energy densities by a 1st to a 4th base frequencies correspondingly, the 1st energy density is between 2.47~6.19, the 2nd energy density is between 2.51~6.28, the 3rd energy density is between 2.49~6.24, and the 4th energy density is between 2.46~6.16; in the 2nd energy wave generation period corresponding to the 2nd set of controls, the 2nd set of energy waves are sequentially a 5th to a 11th energy waves correspondingly with a 5th to a 11th energy densities by a 5th to a 11th base frequencies correspondingly, the 5th energy density is between 2.52~6.29, the 6th energy density is between 2.36~5.89, the 7th energy density is between 2.90~7.25, the 8th energy density is between 2.34~5.85, the 9th energy density is between 2.34~5.85, the 10th energy density is between 2.31~5.78, the 11th energy density is between 2.28~5.70; in the 3rd energy wave generation period corresponding to the 3rd set of controls, the 3rd set of energy waves are sequentially a 12th to a 17th energy waves correspondingly with a 12th to a 17th energy densities by a 12th to a 17th base frequencies correspondingly, the 12th energy density is between 2.23~5.58, the 13th energy density is between 2.37~5.93, the 14th energy density is between 2.79~6.98, the 15th energy density is between 2.89~7.21, the 16th energy density is between 2.21~5.51, the 17th energy density is between 2.77~6.92; in the 4th energy wave generation period corresponding to the 4th set of controls, the 4th set of energy waves are sequentially a 18th to a 23rd energy waves correspondingly with a 18th to a 23rd energy densities by a 18th to a 23rd base frequencies correspondingly, the 18th energy density is between 2.17~5.42, the 19th energy density is between 2.57~6.41, the 20th energy density is between 2.81~7.02, the 21st energy density is between 2.14~5.36, the 22nd energy density is between 2.48~6.21, the 23rd energy density is between 2.43~6.07; in the 5th energy wave generation period corresponding to the 5th set of controls, the 5th set of energy waves are sequentially a 24th to a 28th energy waves correspondingly with a 24th to a 28th energy densities by a 24th to a 28th base frequencies correspondingly, the 24th energy density is between 2.29~5.73, the 25th energy density is between 2.18~5.46, the 26th the energy density is between 2.46~6.15, the 27th energy density is between 1.90~4.75, the 28th energy density is between 1.85~4.63; in the 6th energy wave generation period corresponding to the 6th set of controls, the 6th set of energy waves are sequentially a 29th to a 33rd energy waves correspondingly with a 29th to a 33rd energy densities by a 29th to a 33rd base frequencies correspondingly, the 29th energy density is between 2.08~5.20, the 30th energy density is between 1.41~3.53, the 31st energy density is between 1.33~3.33, the 32nd energy density is between 0.99~2.47, the 33rd energy density is between 2.05~5.13; in the 7th energy wave generation period corresponding to the 7th set of controls, the 7th set of energy waves are sequentially a 34th to a 35th energy waves correspondingly with a 34th to a 35th energy densities by a 34th to a 35th base frequencies correspondingly, the 34th energy density is between 1.45~3.62, the 35th energy density is between 1.39~3.48; in the 8th energy wave generation period corresponding to the 8th set of controls, the 8th set of energy waves are sequentially a 36th to a 37th energy waves correspondingly with a 36th to a 37th energy densities by a 36th to a 37th base frequencies correspondingly, the 36th energy density is between 1.39~3.48, the 37th energy density is between 1.45~3.62; and in the 9th energy wave generation period corresponding to the 9th set of controls, the 9th set of energy waves are sequentially a 38th to a 39th energy waves correspondingly with a 38th to a 39th energy densities by a 38th to a 39th base frequencies correspondingly, the 38th energy density is between 1.79~4.48, and the 39th energy density is between 1.41~3.52.

11. The system as claimed in claim 10, wherein in the controls mode based on the 1st to 4th, 6th, 8th to 11th, 12th, 16th, 18th, 21st, 27th, 28th, 30th to 32nd, and 34th to 37th base frequencies, the D %=70%, the Width=0 Hz, and the TT=7, 15, 19, 24, 35, 37, 37, 39, 42, 47, 49, 51, 53, 72, 76, 106, 110, 133, 144, 144, 144 and 144 secs respectively; in the controls based on the 5th, 13th, 23rd, 24th and 33rd base frequencies, the D %=70%, the Width=1, 1, 3, 2, and 8 Hz, and the TT=36, 46, 56, 60 and 72 secs respectively; in the controls based on the 7th, 14th, 15th, 17th, 20th, 26th and 29th base frequencies, the D %=70%, the Width=7, 7, 9, 7, 9, 6 and 7 Hz respectively, and the TT=30, 45, 57, 45, 57, 65 and 105 secs respectively; in the controls based on the 19th, 22nd, 25th, 38th and 39th base frequencies, the D %=70%, the Width=5, 4, 2, 8, and 2 Hz, and the TT=54, 55, 69, 36 and 12 secs respectively; the 1st to 39th base frequencies are between 18100~18150 Hz, 9900~10100 Hz, 7300~7400 Hz, 4980~5020 Hz, 2100~2150 Hz, 2100~2130 Hz, 1950~2030 Hz, 1860~1880 Hz, 1845~1855 Hz, 1530~1570 Hz, 1220~1250 Hz, 870~890 Hz, 860~880 Hz, 800~820 Hz, 770~785 Hz, 745~765 Hz, 720~740 Hz, 605~620 Hz, 590~610 Hz, 535~560 Hz, 515~535 Hz, 480~495 Hz, 455~475 Hz, 295~310 Hz, 155~170 Hz, 135~150 Hz, 120~135 Hz, 90~110 Hz, 10~20 Hz, 5~25 Hz, 4~15 Hz, 1~6 Hz, 25~45 Hz, 5~20 Hz, 5~15 Hz, 5~8 Hz, 6~15 Hz, 15~28 Hz and 24~35 Hz.

12. The system as claimed in claim 11, wherein the controls based on the 1st to 4th, 6th, 8th to 11th, 12th, 16th, 18th, 21st, 27th, 28th, 30th to 32nd, and 34th to 37th base frequencies are fixed frequency sweep modes respectively; the controls based on the 5th, 13th, 23rd, 24th and 33rd base frequencies are sweep decreasing modes respectively, multiple frequencies being produced and calculated by an adjusted bandwidth equal to 1 Hz based on each base frequency in each sweep decreasing mode; the controls based on the 7th, 14th, 15th, 17th, 20th, 26th and 29th frequency are spread contract modes respectively, multiple frequencies being produced and calculated by an adjusted bandwidth equal to 1 Hz based on each base frequency in each spread contract mode; the controls based on the 19th, 22nd, 25th, 38th and 39th base frequencies are sweep increasing modes respectively, multiple frequencies being produced and calculated by an adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the adjusted bandwidth, the fourth output frequency of the multiple frequencies is calculated as the second output frequency minus the adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the adjusted bandwidth, and when the current output frequency of the multiple frequencies is equal to the base frequency, the current output frequency is the last output frequency.

13. The system as claimed in claim 10, wherein, according to the nine sets of controls, the energy wave generator sequentially outputs a 1st and a 2nd subsequent energy waves correspondingly with a 1st and a 2nd subsequent energy densities by a 1st and a 2nd subsequent base frequencies correspondingly after the 4th energy wave in the 1st energy wave generation period, outputs a 3rd subsequent energy wave with a corresponding 3rd subsequent energy density by a corresponding 3rd subsequent base frequency after the 11th energy wave in the 2nd energy wave generation period, outputs a 4th subsequent energy wave with a corresponding 4th subsequent energy density by a corresponding 4th subsequent base frequency after the 17th energy wave in the 3rd energy wave generation period, outputs a 5th subsequent energy wave with a corresponding 5th subsequent energy density by a corresponding 5th subsequent base frequency after the 23th energy wave in the 4th energy wave generation period, and outputs a 6th subsequent energy wave with a corresponding 6th subsequent energy density by a corresponding 6th subsequent base frequency after the 28th energy wave in the 5th energy wave generation period; wherein, the 1st subsequent energy density is between 2.44~6.10, the 2nd subsequent energy density is between 2.43~6.07, the 3rd subsequent energy density is between 2.25~5.63, the 4th subsequent energy density is between 2.49~6.22, the 5th subsequent energy density is between 2.63~6.58, and the 6th subsequent energy density is between 1.97~4.93; the control based on the 1st subsequent base frequency is a fixed frequency sweep mode, which sets a fixed the 1st subsequent base frequency to a fixed frequency between 4100~4300 Hz with D %=70%, Width (m)=0 Hz and TT=26 secs for a duty cycle; the control based on the 2nd subsequent base frequency is a fixed frequency sweep mode, which sets the 2nd subsequent base frequency to a fixed frequency between 3600~4090 Hz with D %=70%, Width (m)=0 Hz and TT=28 secs for a duty cycle; the control based on the 3rd subsequent base frequency is a fixed frequency sweep mode, which sets the 3rd subsequent base frequency to a fixed frequency between 1000~1100 Hz with D %=70%, Width (m)=0 Hz and TT=44 secs for a duty cycle; the control based on the 4th subsequent base frequency is a sweep decreasing mode, which sets effect frequencies decreasingly adjusted based on the 4th subsequent base frequency between 680~720 Hz with D %=70%, Width=3 Hz, adjusted bandwidth equal to 1 Hz, and TT=48 seconds for a duty cycle; the control based on the 5th subsequent base frequency is a sweep increasing mode, which sets effect frequencies increasingly adjusted based on the 5th subsequent base frequency between 400~450 Hz with D %=70%, Width (m)=9 Hz, adjusted bandwidth=1 Hz and TT=60 secs for a duty cycle; and the control based on the 6th subsequent base frequency is a sweep decreasing mode, which sets effect frequencies decreasingly adjusted based on the 6th subsequent base frequency between 60~95 Hz with D %=70%, Width=1 Hz, adjusted bandwidth equal to 1 Hz, and TT=78 seconds for a duty cycle.

14. A method for relieving hypertension, comprising the steps of: providing the system as claimed in claim 1; and by the multiple controls of the energy wave's frequency control mode acting on the energy wave generator to generate and emit energy waves each with a corresponding energy density in each corresponding energy wave generation period, wherein the energy density of each energy wave being calculated by a corresponding base frequency between 1~18150 Hz, a sweep bandwidth (Width) of the corresponding base frequency, an emission rate (D %) and a total time of emission (TT) in a duty cycle, so that the energy waves with the corresponding energy densities within values of 0.99~7.25 effecting on a body of animal or human to relieve hypertension, and wherein the value of the energy density of each energy wave based on the corresponding base frequency being calculated by the formula of ED=log 10 (base freq.×D %×(2Width+1)×(TT)+1).

15. The method as claimed in claim 14, wherein the multiple controls are nine sets, the multiple energy wave generation periods are nine sequentially from a 1st to a 9th corresponding to the nine sets of controls a 1st to a 9th, so as to act on the energy wave generator to sequentially output nine sets of energy waves from a 1st to a 9th with corresponding nine sets of energy densities between 2.46~6.28, 2.28~7.25, 2.21~7.21, 2.14~7.02, 1.85~6.15, 0.99~5.20, 1.39~3.62, 1.39~3.62 and 1.41~4.48; there is a non-energy period between every two adjacent energy wave generation periods, the energy wave generator generates at least one base frequency in the non-energy period and filters at least one energy density of the at least one base frequency to zero.

16. The method as claimed in claim 15, wherein in the 1st energy wave generation period corresponding to the 1st set of controls, the 1st set of energy waves are sequentially a 1st to a 4th energy waves correspondingly with a 1st to a 4th energy densities by a 1st to a 4th base frequencies correspondingly, the 1st energy density is between 2.47~6.19, the 2nd energy density is between 2.51~6.28, the 3rd energy density is between 2.49~6.24, and the 4th energy density is between 2.46~6.16; in the 2nd energy wave generation period corresponding to the 2nd set of controls, the 2nd set of energy waves are sequentially a 5th to a 11th energy waves correspondingly with a 5th to a 11th energy densities by a 5th to a 11th base frequencies correspondingly, the 5th energy density is between 2.52~6.29, the 6th energy density is between 2.36~5.89, the 7th energy density is between 2.90~7.25, the 8th energy density is between 2.34~5.85, the 9th energy density is between 2.34~5.85, the 10th energy density is between 2.31~5.78, the 11th energy density is between 2.28~5.70; in the 3rd energy wave generation period corresponding to the 3rd set of controls, the 3rd set of energy waves are sequentially a 12th to a 17th energy waves correspondingly with a 12th to a 17th energy densities by a 12th to a 17th base frequencies correspondingly, the 12th energy density is between 2.23~5.58, the 13th energy density is between 2.37~5.93, the 14th energy density is between 2.79~6.98, the 15th energy density is between 2.89~7.21, the 16th energy density is between 2.21~5.51, the 17th energy density is between 2.77~6.92; in the 4th energy wave generation period corresponding to the 4th set of controls, the 4th set of energy waves are sequentially a 18th to a 23rd energy waves correspondingly with a 18th to a 23rd energy densities by a 18th to a 23rd base frequencies correspondingly, the 18th energy density is between 2.17~5.42, the 19th energy density is between 2.57~6.41, the 20th energy density is between 2.81~7.02, the 21st energy density is between 2.14~5.36, the 22nd energy density is between 2.48~6.21, the 23rd energy density is between 2.43~6.07; in the 5th energy wave generation period corresponding to the 5th set of controls, the 5th set of energy waves are sequentially a 24th to a 28th energy waves correspondingly with a 24th to a 28th energy densities by a 24th to a 28th base frequencies correspondingly, the 24th energy density is between 2.29~5.73, the 25th energy density is between 2.18~5.46, the 26th the energy density is between 2.46~6.15, the 27th energy density is between 1.90~4.75, the 28th energy density is between 1.85~4.63; in the 6th energy wave generation period corresponding to the 6th set of controls, the 6th set of energy waves are sequentially a 29th to a 33rd energy waves correspondingly with a 29th to a 33rd energy densities by a 29th to a 33rd base frequencies correspondingly, the 29th energy density is between 2.08~5.20, the 30th energy density is between 1.41~3.53, the 31st energy density is between 1.33~3.33, the 32nd energy density is between 0.99~2.47, the 33rd energy density is between 2.05~5.13; in the 7th energy wave generation period corresponding to the 7th set of controls, the 7th set of energy waves are sequentially a 34th to a 35th energy waves correspondingly with a 34th to a 35th energy densities by a 34th to a 35th base frequencies correspondingly, the 34th energy density is between 1.45~3.62, the 35th energy density is between 1.39~3.48; in the 8th energy wave generation period corresponding to the 8th set of controls, the 8th set of energy waves are sequentially a 36th to a 37th energy waves correspondingly with a 36th to a 37th energy densities by a 36th to a 37th base frequencies-correspondingly, the 36th energy density is between 1.39~3.48, the 37th energy density is between 1.45~3.62; and in the 9th energy wave generation period corresponding to the 9th set of controls, the 9th set of energy waves are sequentially a 38th to a 39th energy waves correspondingly with a 38th to a 39th energy densities by a 38th to a 39th base frequencies correspondingly, the 38th energy density is between 1.79~4.48, and the 39th energy density is between 1.41~3.52.

17. The method as claimed in claim 16, wherein in the controls made based on the 1st to 4th, 6th, 8th to 11th, 12th, 16th, 18th, 21st, 27th, 28th, 30th to 32nd, and 34th to 37th base frequencies, the D %=70%, the Width=0 Hz, and the TT=7, 15, 19, 24, 35, 37, 37, 39, 42, 47, 49, 51, 53, 72, 76, 106, 110, 133, 144, 144, 144 and 144 secs respectively; in the controls based on the 5th, 13th, 23rd, 24th and 33rd base frequencies, the D %=70%, the Width=1, 1, 3, 2, and 8 Hz, and the TT=36, 46, 56, 60 and 72 secs respectively; in the controls based on the 7th, 14th, 15th, 17th, 20th, 26th and 29th base frequencies, the D %=70%, the Width=7, 7, 9, 7, 9, 6 and 7 Hz respectively, and the TT=30, 45, 57, 45, 57, 65 and 105 secs respectively; in the controls based on the 19th, 22nd, 25th, 38th and 39th base frequencies, the D %=70%, the Width=5, 4, 2, 8, and 2 Hz, and the TT=54, 55, 69, 36 and 12 secs respectively; the 1st to 39th base frequencies are between 18100~18150 Hz, 9900~10100 Hz, 7300~7400 Hz, 4980~5020 Hz, 2100~2150 Hz, 2100~2130 Hz, 1950~2030 Hz, 1860~1880 Hz, 1845~1855 Hz, 1530~1570 Hz, 1220~1250 Hz, 870~890 Hz, 860~880 Hz, 800~820 Hz, 770~785 Hz, 745~765 Hz, 720~740 Hz, 605~620 Hz, 590~610 Hz, 535~560 Hz, 515~535 Hz, 480~495 Hz, 455~4751 Hz, 295~310 Hz, 155~170 Hz, 135~150 Hz, 120~135 Hz, 90~110 Hz, 10~20 Hz, 5~25 Hz, 4~15 Hz, 1~6 Hz, 25~45 Hz, 5~20 Hz, 5~15 Hz, 5~81 Hz, 6~15 Hz, 15~28 Hz and 24~35 Hz respectively.

18. The method as claimed in claim 16, wherein, by the nine sets of controls, the energy wave generator sequentially outputs a 1st and a 2nd subsequent energy waves correspondingly with a 1st and a 2nd subsequent energy densities by a 1st and a 2nd subsequent base frequencies correspondingly after the 4th energy wave in the 1st energy wave generation period, outputs a 3rd energy wave with a corresponding 3rd subsequent energy density by a corresponding 3rd subsequent base frequency after the 11th energy wave in the 2nd energy wave generation period, outputs a 4th subsequent energy waves with a corresponding 4th subsequent energy density by a corresponding 4th subsequent base frequency after the 17th energy wave in the 3rd energy wave generation period, outputs a 5th subsequent energy wave with a corresponding 5th subsequent energy density by a corresponding 5th subsequent base frequency after the 23th energy wave in the 4th energy wave generation period, and outputs a 6th subsequent energy wave with a corresponding 6th subsequent energy density by a corresponding 6th subsequent base frequency after the 28th energy wave in the 5th energy wave generation period; wherein, the 1st subsequent energy density is between 2.44~6.10, the 2nd subsequent energy density is between 2.43~6.07, the 3rd subsequent energy density is between 2.25~5.63, the 4th subsequent energy density is between 2.49~6.22, the 5th subsequent energy density is between 2.63~6.58, and the 6th subsequent energy density is between 1.97~4.93; the control based on the 1st subsequent base frequency is a fixed frequency sweep mode, which sets the 1st subsequent base frequency to a fixed frequency between 4100~4300 Hz with D %=70%, Width (m)=0 Hz and TT=26 secs for a duty cycle; the control based on the 2nd subsequent base frequency is a fixed frequency sweep mode, which sets the 2nd subsequent base frequency to a fixed frequency between 3600~4090 Hz with D %=70%, Width (m)=0 Hz and TT=28 secs for a duty cycle; the control based on the 3rd subsequent base frequency is a fixed frequency sweep mode, which sets a fixed the 3rd subsequent base frequency to a fixed frequency between 1000~1100 Hz with D %=70%, Width (m)=0 Hz and TT=44 secs for a duty cycle; the control based on the 4th subsequent base frequency is a sweep decreasing mode, which sets effect frequencies decreasingly adjusted based on a 4th subsequent base frequency between 680~720 Hz with D %=70%, Width=3 Hz, adjusted bandwidth equal to 1 Hz, and TT=48 seconds for a duty cycle; the control based on the 5th subsequent base frequency is a sweep increasing mode, which sets effect frequencies increasingly adjusted based on the 5th subsequent base frequency between 400~450 Hz with D %=70%, Width (m)=9 Hz, adjusted bandwidth=1 Hz and TT=60 secs for a duty cycle; and the control based on the 6th subsequent base frequency is a sweep decreasing mode, which sets effect frequencies decreasingly adjusted based on DB the 6th subsequent base frequency between 60~95 Hz with D %=70%, Width=1 Hz, adjusted bandwidth equal to 1 Hz, and TT=78 seconds for a duty cycle.

\* \* \* \* \*